United States Patent [19]
Marchand et al.

[11] Patent Number: 5,217,905
[45] Date of Patent: Jun. 8, 1993

[54] DEVICE AND METHOD FOR THE RAPID QUALITATIVE AND QUANTITATIVE DETERMINATION OF THE PRESENCE OF A REACTIVE LIGAND IN A FLUID

[75] Inventors: Joseph Marchand, Verrieres Le Buisson; Jacques Toledano, Paris, both of France

[73] Assignees: Compagnie Oris Industrie S.A., Gif-Sur-Yvette; Cistest, Paris, both of France

[21] Appl. No.: 220,895

[22] Filed: Jul. 18, 1988

[30] Foreign Application Priority Data

Apr. 28, 1988 [FR] France ............... 88 05668

[51] Int. Cl.⁵ .................. G01N 33/53; G01N 33/558
[52] U.S. Cl. ...................... 436/518; 422/56;
422/57; 422/58; 435/7.92; 435/7.93; 435/805;
435/969; 435/970; 435/971; 436/170; 436/805;
436/810
[58] Field of Search ............ 436/810, 170, 805, 518;
435/7.92, 7.93, 805, 960, 969, 970, 971; 422/56, 58, 57

[56] References Cited

U.S. PATENT DOCUMENTS

| | | | |
|---|---|---|---|
| 4,446,232 | 5/1984 | Liotta | 435/805 |
| 4,522,786 | 6/1985 | Ebersole | 422/56 |
| 4,668,619 | 5/1987 | Greenquist et al. | 422/56 |
| 4,743,542 | 5/1988 | Graham, Jr. et al. | 436/534 X |
| 4,791,055 | 12/1988 | Boguzlash et al. | 436/546 X |
| 4,803,170 | 2/1989 | Stanton et al. | 436/514 X |

Primary Examiner—David Saunders
Assistant Examiner—Christopher L. Chin
Attorney, Agent, or Firm—Browdy and Neimark

[57] ABSTRACT

A device for the rapid qualitative and quantitative determination of the presence of a reactive ligand in a fluid.

This device comprises a first reaction zone in which there is an at least temporarily impermeable membrane designed to receive a sample of test fluid and to be associated with at least one labeled reagent; a second reaction zone which is bounded on the one hand by the said membrane and on the other by a second at least temporarily impermeable membrane comprising a solid phase containing a reference reagent; and a third reaction zone which contains means for developing the reaction.

A method for the rapid qualitative and quantitative determination of the presence of a reactive ligand in a fluid.

Applications to the detection of the presence, in a biological fluid, of antibodies or antigens in particular.

20 Claims, 3 Drawing Sheets

DEVICE AND METHOD FOR THE RAPID QUALITATIVE AND QUANTITATIVE DETERMINATION OF THE PRESENCE OF A REACTIVE LIGAND IN A FLUID

The present invention relates to a device and a method for the rapid qualitative and quantitative determination of a reactive ligand present in a fluid. The invention applies more particularly, but without implying a limitation, to the detection of the presence of antibodies or antigens in a biological fluid, to the detection of toxic substances, viruses or bacteria in a fluid of any kind (water, fluid products from the agri-foodstuffs industries, industrial effluents, biological fluids, etc.) and to the chemical assay of substances (such as hormones, vitamins, enzymes, drugs, etc.) present in a fluid (especially a biological fluid).

Immunological methods for the determination of the presence of concentration of antigenic substances in biological fluids are now well known; they are based on the formation of a complex between the antigenic substance to be determined and one or more antibodies, it being possible for one of the components of the complex to be labeled with a radioactive element (for example $^{125}I$) so that it can be detected and/or quantitatively analyzed after separation of the complexed labeled antigen or antibody from the non-complexed labeled antigen or antibody.

In the methods of immunological determination by competition, the antigenic substance contained in the sample of liquid for analysis competes with a known quantity of labeled antigen for a limited number of antibody binding sites; the quantity of labeled antigen bound to the antibody is inversely proportional to the quantity of antigen contained in the sample.

Immunometric tests use a labeled antibody; the quantity of labeled antibody associated with the complex is proportional to the quantity of antigenic substance contained in the sample.

Immunometric tests which are particularly suitable for the detection of polyvalen antigens, i.e. antigenic substances capable of complexing with at least two antibodies at the same time, involve the use of a quantity of unlabeled antibody bound to a solid support which is unsoluble in the liquid for analysis, and a quantity of soluble antibody carrying an indicator, such as a radioactive isotope, which permits the detection of quantitative determination of the ternary complex formed between the antibody in the solid phase, the antigen and the labeled antibody. These methods initially involve bringing the antibody bound to the solid phase into contact with the sample for analysis in order to extract the antigen from the sample by the formation of a binary complex between the antibody in the solid phase and the antigen. After a period of incubation, the solid support is washed to remove the residue of liquid sample, including any unreacted antigen, and then brought into contact with a solution containing a known quantity of labeled antibody. After a second period of incubation to allow the labeled antibody to complex with the antigen bound to the solid support via the unlabeled antibody, the solid support is washed a second time to remove the unreacted labeled antibody, after which the presence of labeled antibody on the washed solid support is detected (for example by measuring the radiation emitted in cases where the indicator is a radioactive element) and, if appropriate, the labeled antibody is subjected to a process of quantitative determination.

These methods are known as sandwich or bi-site methods because the antigen carries two antibodies bound to its surface of two different sites. They are described by WIDE in "Radioimmunoassay Methods" (Kirkham and Hunter, published by E. and S. Livingstone, Edinburgh, 1970, p. 199–206). Specific applications (test for detecting the antigen bound to hepatitis virus) are described in U.S. Pat. No. 3,867,517; variants of these methods ("simultaneous" or "inverse" variants) are described by JEONG et al. in "Comparison of RIA with a single-incubation two-site immunoradiometric assay (IRMA) as applied to the determination of human thyroid stimulation hormone (HTSH)", Bio-Rad Laboratories, 1979; in U.S. Pat. No. 4,174,384 (labeling of two antibodies with a fluorescent chromophore (fluorescein) and with a chromophore with absorbs the light emitted by fluorescein); and in U.S. Pat. No. 4,098,876. These methods initially used polyclonal antibodies which are insufficiently sensitive because of the existence of a cross reactivity with other antigens. French patent no. 81 16030 to HYBRITECH, published under no. 2 487 983, proposes replacing the polyclonal antibodies with monoclonal antibodies, in these immunometric tests, in order substantially to increase the sensitivity of these methods.

French patent no. 82 16973 to LIOTTA, published under no. 2 514 511, describes a device and a method, namely the ELISA method, for determining the presence of antigens in biological fluids, eliminating the dilution and washing operations which the method requires and shortening the duration of the incubation period. The device proposed comprises a matrix formed of a strip of nitrocellulose or diazobenzyloxymethyl (DBM) paper in a porous gel, such as polyacrylamide, agarose or collagen, it being possible for the antigen to be trapped in the pores of the gel or to be crosslinked with the gel via the amine groups of the ligand and the carboxyl groups carried by the matrix, or formed of a strip of cellulose or plastic fibers, inside which particles or beads containing the ligand are trapped. According to this LIOTTA patent, the device comprises: a first zone which contains antigens and antibodies bound to an enzyme, these antibodies being located in the said first zone so that they are removed from this first zone when they have reacted with antigens (non-bound) contained in the test sample, passing through this first zone, but so that they are not removed when such antigens are absent, —and a second zone which contains a substance capable of reacting with the said antibodies bound to an enzyme, in order to produce a color reaction disclosing the presence of the said antibodies. Specifically, the immunoassay device described in the LIOTTA patent comprises a laminate with three porous layers of matrix, the first layer being impregnated with a specific antibody bound to an enzyme, the second porous layer containing an immobilized (bound) reference antigen and the third layer containing a color-producing substrate which reacts with the enzyme bound to the antibody. When brought into contact with the first layer, the free antigen to be assayed, present in the sample for analysis, diffuses into the second and then into the third layer. The free antigen present in the sample competes with the bound reference antigen, immobilized in the second layer, to combine with the antibody bound to an enzyme. If the antibody bound to an enzyme combines with the free antigen, it diffuses freely into the third layer and produces a color reaction. If, on the other hand, the sample for analysis does not contain antigen, all the antibodies bound to an enzyme possess free binding sites and combine with the immobilized antigen present in the second layer, the antibody bound to an enzyme, which combines with the antigen immobilized in the second layer, does not diffuse into the third layer and no color reaction is produced. French patent 87 08007 to LIOTTA, published under no. 2 599 845, describes a variant of this device which comprises only two layers, the upper layer carrying the antigen with the two reactive antibodies and the lower layer containing a chromogenic substrate, it also being possible for the two zones, i.e. the trapping zone and the substrate zone, to be juxtaposed. The porous layers through which the antigen in the sample, combined with the antibody bound to an enzyme, diffuses therefore act as a selective filter which only lets through the antigen combined with the enzyme-labeled antibody, but does not function if the antibody is not combined with antigen, i.e. when antigen is absent.

U.S. Pat. No. 4,632,901 to HYBRITECH (and corresponding PCT international application no. 85/05451) describes a method and a device for carrying out immunoassays which do not involve lengthy incubation steps associated with several washings, and which, by virtue of their simplicity, can be used by the doctor in his surgery of even by the patient at home. The device in question comprises a first, porous component which consists of a membrane or filter to which a monoclonal or polyclonal antibody is bound, the said antibody recognizing the antigen which is to be identified, and a second, absorbent component which has capillary passages perpendicular to its upper and lower surfaces; this second component is in capillary communication with the porous membrane, or the like, forming the first component of the device, and its pore size is such as to induce liquid to pass through the first component without the application of external means. The porous filter membrane can be made of Nylon carrying $NH_2$ groups to which the antibodies are covalently bonded by coupling with the aid of glutaraldehyde, and the absorbent component can be made of a fibrous filter material such as fibers of cellulose acetate, polyester, polyolefin, etc. These two components can be separated from one another by another porous component (made of polyethylene for example) which does not bind antibodies non-specifically and prevents labeled antibody from binding non-specifically to the upper surface of the absorbent component.

Similarly, European patent application no. 186 100 ABBOTT LABORATORIES describes a device for determining the presence or quantity of a substance in a test sample, the said device comprising a non-absorbent, porous fibrous matrix, such as glass, impregnated with a hydrophobic polymer which forms a surface coating over at least part of the matrix and to which reagent, for example an antibody or an antigen, is bound which is capable of reacting with the substance to be identified in the sample, it being possible for this device to be associated with an underlying layer of absorbent material and/or with a layer of fibrous material, such as glass fibers or cellulose filter paper, which covers the fibrous matrix and can act as a "prefilter".

European patent application no. 206 561 to MUREX CORPORATION also discloses a diagnostic device which comprises a filter component having at least one reaction zone associated with at least one peripheral zone, an absorbent component associated solely with the peripheral zone of the first component, and a component for holding the filter in the appropriate position. The "reaction" which takes place in the reaction zone can equally well be a separation by filtration as an immunological coupling, and the signals for reading the reaction appear in the same zone. The liquid test sample arrives on the filter through a funnel whose discharge orifice is calculated so that its diameter is sufficient, in conjunction with the pressure of the liquid in the funnel, for the liquid to discharge onto the upper surface of the filter but not to pass through the latter, the hydrostatic pressure subsequently being adjusted so that the liquid penetrates the filter under gravity and diffuses through the latter under capillary action without passing right through it perpendicularly.

A common feature of all these devices is the presence of a porous filter component through which the liquid test sample flows, means being provided, if appropriate, for slowing down the liquid flow. However, this type of filter component does not allow sufficient contact time between the reagent bound to the filter component and the substance to be identified in the liquid sample, and therefore does not make it possible to obtain a reaction whose sensitivity is such that it is capable of detecting very low concentrations of the said substance in the sample; furthermore, the flow of the sample containing, if appropriate, a ligand-receptor complex, such as an antigen-antibody complex in particular, through a filter component is liable to generate reading errors.

The object of the present invention was consequently to provide a device and a method for the rapid qualitative and quantitative determination of the presence of a reactive ligand in a fluid, which device and method meet practical needs better than the devices and methods proposed for the same purpose in the prior art, especially insofar as the device according to the invention is very much more sensitive than those indicated in the prior art since it is able to detect very low concentrations of ligand, especially antigen, in a fluid, especially a biological fluid, these concentrations possibly being as low as 5 picograms, whereas the methods of the prior art do not enable such low concentrations to be detected and only start to be sensitive at a few $\mu g$; insofar as it makes it possible to perform two reactions between a reagent and a substance to be detected, in two totally separate places, which gives rise to very specific reactions and thereby definitely avoids cross reactions and false positives or negatives without resorting to competitive methods; insofar as it is capable of using several types of monoclonal antibodies simultaneously and is applicable to all the methods of reading the results, such as colorimetry, fluorescence, chemoluminescence, radioactivity, etc.; and insofar as it makes it possible to perform quantitative assays.

The present invention relates to a device for the rapid qualitative and quantitative determination of the presence of a reactive ligand in a fluid, of the type comprising a reaction zone containing a labeled reagent, especially a labeled antibody or antigen, for reacting with the ligand to be identified, and a disclosure zone, the said device comprising, in combination:

a first reaction zone comprising an at least temporarily impermeable membrane which is intended to receive a sample of test fluid and to be associated with at least one appropriately labeled reagent capable of recognizing the ligand or ligands to be identified which may be present in the said sample, and with means for rendering the said membrane permeable;

a second reaction zone, separate from the first and at least temporarily isolated therefrom by the above-mentioned membrane, comprising a solid phase bound to an unlabeled reference reagent capable of recognizing and retaining the labeled reagents from the first zone which have not bound to the ligand or ligands to be identified, and at least temporarily closed, on the opposite side to the first membrane, by a second at least temporarily impermeable membrane; and a third reaction zone at least temporarily isolated from the above-mentioned second reaction zone by the said second membrane, containing means for disclosing the presence or absence of the labeled reagent.

In one advantageous embodiment of the device according to the present invention, at least one of the above-mentioned two membranes is made of a material which is impermeable for a first period of time sufficient to enable the reaction, which is to occur in the reaction zone in question, to take place, the said material being such that it is rendered permeable after this first period of time so as to allow products of the reaction which has taken place to pass through into the next reaction zone.

In another embodiment of the device according to the present invention, the means for rendering one or more membranes permeable are independent of the membrane in question.

In yet another advantageous embodiment of the device according to the present invention, the means for rendering one or more membranes permeable are incorporated in the membrane in question.

In one advantageous arrangement of the invention, the said means for rendering one or more membranes permeable consist of a substance for dissolving the said membrane or membranes.

In another advantageous arrangement of the invention, the said means for rendering one or more membranes permeable consist of an agent for lysing the said membrane or membranes.

In yet another advantageous arrangement of the invention, the at least temporarily impermeable materials used to produce the above-mentioned membrane or membranes are selected from the group comprising, in particular, carbohydrates and gelatin.

In another advantageous embodiment of the device according to the present invention, the first reaction zone is suitable for receiving, in a solid form, advantageously supported by the first membrane, at least one appropriately labeled reagent, if appropriate in association with an agent for lysing the said membrane.

According to the invention, the labeled reagent is appropriately labeled, especially with an enzyme, a radioisotope of a fluorescent or chemoluminescent chromophoric chemical, and it can advantageously be an antibody or an antigen.

Also according to the invention, the material which constitutes at least the first membranes is such that the latter is dissolved after an appropriate time by the aqueous liquid phase of the test sample.

According to the present invention, the agent for rendering the membrane permeable consists of an agent, such as an appropriate enzyme, for lysing the membrane in question, which can either by incorporated in the latter, or associated with the said membrane by introduction into the device according to the invention, or associated with the solid form which comprises the above-mentioned reagent.

In yet another advantageous embodiment of the device according to the present invention, the solid phase bound to an unlabeled reference reagent, present in the second reaction zone, consists of an insoluble support to which the unlabeled reagent (especially antibody or antigen) is bound, the unlabeled reagent corresponding to the ligand to be detected and, the insoluble support being selected from the group comprising, in particular, microspheres, microplates and the like.

In one advantageous embodiment of the device according to the present invention, the third reaction zone contains a chromogenic substrate when it is intended that the reaction be read by colorimetry.

In another advantageous embodiment of the device according to the present invention, the device has, between the first and second reaction zones, an intermediate zone comprising a labeled reagent, in which case the first reaction zone comprises an unlabeled reagent.

In one advantageous arrangement of this embodiment, the intermediate zone comprises at least one layer of multilayer vesicular structures incorporating at least one reagent which is capable of being released after an appropriate time by an appropriate lyzing agent such as, in particular, an enzyme.

In another advantageous arrangement of this embodiment, the intermediate zone is formed of an intermediate membrane intercalated between the above-mentioned first membrane and the second reaction zone, the said intermediate membrane advantageously being associated with a labeled reagent, in which case the first membrane is associated with the same kind of reagent as the above-mentioned intermediate membrane.

The embodiment of the device according to the invention which has three reaction zones makes it possible to carry out qualitative determinations of the presence or absence of reactive ligands in a fluid, especially antigens or antibodies in a biological fluid. The embodiment of the device according to the invention which has an additional zone makes it possible to carry out semi-quantitative assays of such ligands.

According to the present invention, it is also possible to carry out quantitative assays by associating the third zone of the device with a quantifying apparatus known per se, such as RIA, spectrophotometer, etc.

In one advantageous embodiment of the device according to the present invention, the above-mentioned reaction zones are superimposed to form an upper stage containing the first reaction zone, a middle stage containing the second reaction zone and a lower stage containing the third reaction zone, and, if appropriate, an intermediate stage, between the upper stage and the middle stage, containing the intermediate reaction zone.

The present invention also relates to a method for the rapid qualitative and quantitative determination of the presence of a reactive ligand in a fluid, wherein, in a first step, a sample of the fluid for analysis is brought into contact with a labeled reagent, such as a labeled antibody or antigen in particular, in a zone which is temporarily isolated from the zones in which the subsequent steps of the process take place, for a sufficient time to enable the ligand-reagent reaction to occur, after which the isolation of the zone in which the said reaction has taken place is broken so as to allow any reaction product to come into contact, in a second step, with a second, unlabeled reagent corresponding to the ligand which is to be identified in the above-mentioned sample of fluid, in a second zone which is temporarily isolated from the following zone, after which the isolation of the second zone is broken so as to allow the product of the first or second reaction to come into contact, in the third step of the process, with means for disclosing the presence—or absence—of the ligand to be detected.

In one way of carrying out the method according to the present invention, the sample of fluid is brought into contact with an unlabeled reagent in the first step of the process, and the second step of the process is preceded by an intermediate step in which the ligand-unlabeled reagent complex formed in the first step is brought into contact with a labeled reagent of the same kind as the reagent used in the first step, in a zone which is temporarily isolated from the next step.

In an advantageous method of this way of carrying out the invention, the unlabeled reagent brought into contact with the sample of fluid for analysis in the first step of the process is introduced in a given quantity corresponding to a known quantity of ligand, such as the one to be detected, and the excess ligand, i.e. the ligand not bound to the reagent in the first step, is trapped, in the intermediate step of the process, by the labeled reagent to which the said excess ligand binds; as a result, the reaction for disclosing the possible presence of the ligand in the fluid for analysis is only positive if the amount for ligand in the said fluid is greater than the above-mentioned quantity, thereby permitting a semi-quantitative determination of the ligand present in the said fluid.

In a preferred way of carrying out the method according to the present invention, the first step of the process if an absorption phase, the second step of the process is a desorption phase and the third step of the process is an absorption phase.

When the method according to the invention includes an intermediate step intercalated between the first and second steps of the process, this intermediate step is an absorption phase like the first step.

In addition to the foregoing provisions, the invention also includes other provisions which will become apparent from the following description.

The invention will be understood more clearly with the help of the following additional description, which refers to the attached drawings; in these drawings.

Figure 1:
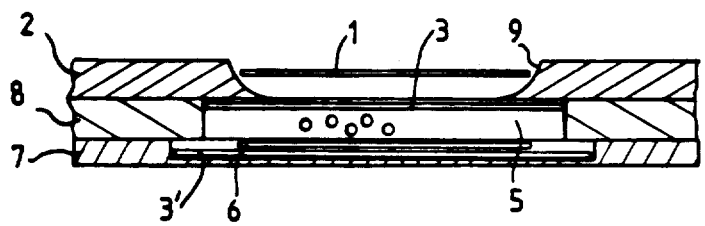
FIG. 1 is a schematic representation, in orthogonal section, of an embodiment of the device according to the present invention.

It must be clearly understood, however, that these drawings and the corresponding descriptive sections are given solely in order to illustrate the subject of the invention, without in any way implying a limitation.

The device according to the present invention, shown in FIG. 1, comprises, from bottom to top, a support 7 carrying a pellet of chromogenic substrate 6, above which there is a membrane 3' which will be described in greater detail later. Above this membrane 3' there is a layer of microspheres 5 which will be described in greater detail in the remainder of the present specification. The microspheres are advantageously, although not necessarily, protected on either side by protective layers which can be made of any suitable material, especially textile. There is a second membrane, 3, above the layer of microspheres 5; the framework of the device is formed by the structure 2 together with the support 7 and an intermediate frame 8. Inserted in the cupular indentation 9 in the structure 2, there is a pellet 1, preferably lyophilized, of a reagent which recognizes the ligand to be detected with the aid of the device according to the present invention. The device further comprises an intermediate zone 4 for performing semiquantitative determinations.

The ligands to be detected with the aid of this device are antigens and antibodies, as well as all kinds of chemical or biological substances. There are a very large number of applications of the method and device according to the present invention; among these applications, there may be mentioned: the diagnosis of viral and microbial complaints, enzyme assays, the detection of autoimmune diseases and Alzheimer's disease, the early detection of cancers, rapid blood grouping, the assay of drugs in the bloodstream, the detection of allergens and the diagnosis of allergies, the assay of membrane receptors, hormone assays and the assay of chemical elements, especially the anions and cations in the electropherogram. Of course, this list is not exhaustive and does not imply a limitation.

The reagents which recognize the ligand to be detected are essentially antibodies or antigens, which are preferably used in the lyophilized state in the form of pellets 1.

The antibodies or antigens contained in the pellet 1 are antibodies or antigens labeled with an appropriate label such as a radioisotope, an enzyme, a fluorescent substrate, a chemical capable of giving a color reaction with an appropriate substrate, etc.

The membrane 3 forming the upper stage of the device is made of a material which is temporarily impermeable for a sufficient time to allow a drop of the sample of fluid to be examined, brought into contact with the pellet 1, to react and, if the fluid does indeed contain the ligand to be detected, to form a ligand-labeled antibody or antigen complex, the membrane 3 losing its impermeability after this time and allowing all the fluid, which may or may not contain the above-mentioned complex, to pass through to the middle stage.

The membrane 3 is advantageously made of gelatin, which is impermeable under normal conditions but which is dissolved within 20 seconds to 1 minute by an appropriate enzyme such as collagenase. The enzyme for lysing the gelatin is advantageously included in the pellet 1 of antibody or antigen because the time required for the ligand and the reagent (antibody or antigen) contained in the pellet 1 to react with one another is of the same order as the time required by the lysing enzyme to dissolve the membrane 3. It may be advantageous to strengthen the gelatin membrane 3 by embedding a glass fiber structure therein, which forms the skeleton of the membrane 3 after the gelatin has dissolved.

The middle stage of the device according to the present invention comprises a layer 5 of microspheres made of any appropriate material such as a metal or metal alloy, polyacrylamide, etc., with diameters varying between 10 and 250 $\mu$m, the said microspheres carrying a reagent (antigen or antibody) identical or similar to the ligand to be detected, the purpose of which is to retain the labeled reagents which have remained free in the upper stage.

Under these conditions, if one is testing for an antigen in a drop of biological fluid, the sequence of events in the case of a positive reaction is as follows: the antigen present in the said fluid binds to the antibody contained in the pellet 1, on the membrane 3, which is dissolved by an appropriate enzyme as soon as the above reaction has taken place; the fluid containing the above-mentioned antigen-antibody complex passes through the layer of microspheres 5, without being retained by the latter, and then reaches the membrane 3', which it dissolves by means of the collagenase contained in the said fluid, thereby allowing the fluid to pass into the disclosure zone containing a substrate 6, which is colored on contact with the fluid examined.

In the case of a negative reaction, i.e. if the fluid examined does not contain antigen, the labeled antibody of the upper stage is retained by the unlabeled antigen bound to the microspheres, and therefore does not color the substrate.

The methods are the same, mutatis mutandis, if one is testing for an antibody in the fluid.

If it is desired to carry out a semiquantitative determination, the reagent of the upper stage is unlabeled and the upper stage is followed by an intermediate stage 4 comprising multilayer vesicular structures or microcapsules, inside which labeled reagents are incorporated. The reagent associated with the pellet 1, for example an antibody, is introduced in a quantity which corresponds to a given quantity of antigen, say x ng/ml of antigen, for example 10 ng/ml of antigen. If the test fluid contains a greater quantity of antigen, the excess is bound to the labeled antibodies incorporated in the vesicular structures of the intermediate stage as soon as these structures open under the action of the lysing enzyme, whereby the results obtained are relative to a threshold, i.e. they are semiquantitative results.

Figure 2:
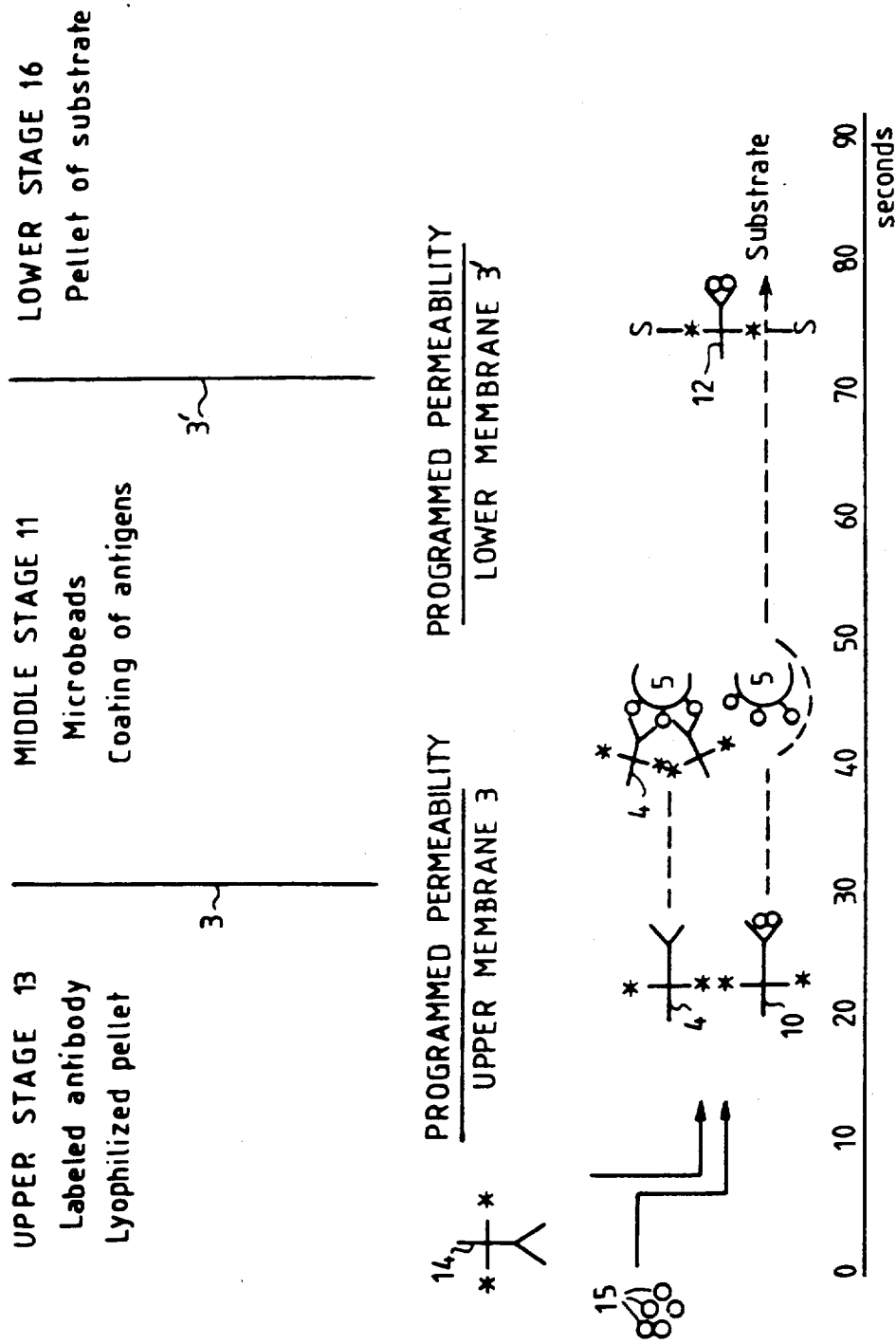
FIG. 2 shows a diagram of the steps of the method for the qualitative determination of the presence of antigens.

FIG. 2 illustrates the qualitative assay of antigens where a positive reaction is obtained: it shows that the antibody-antigen complex formed, designated by reference 10, passes through the middle stage, without being retained on the microspheres, to give a positive reaction. In fact, all the labeled antibodies 14 of the pellet 1 are saturated by the antigens 15 present in the serum, after about 30 seconds, so that when, after lysis of the upper membrane 3, i.e. after these 30 seconds, the saturated complex 10 reaches the microspheres of the layer 5 to which antigens of the same kind as those to be detected in the serum are bound, the microspheres cannot bind theses saturated complexes, which pass into the disclosure zone through the lysed membrane 3'.

More specifically, the assay illustrated in FIG. 2 can be applied to the qualitative assay of the presence of syphilis antigens.

The labeled antibodies 14 constituting the reagent of the upper stage 13 are human IgGs (500 picograms) originating from positive control sera (Pasteur Code 76751) and labeled with peroxidase (Merck) on concanavalin A (method of GUESDON AND AV-RAMEAS, 1980). the pellet which contains the reagent also contains 5 units of collagenase (Collagenase Clostridium from Calbiochem). The membrane 3 is a 10 μm thick polycarbonate-DMF membrane with 3 μm pores which are blocked with a hot 3% ethanolic solutions of gelatin, the gelatin which blocks the pores being lysed by the collagenase after 30 seconds. The membrane 3 is supported by a glass fiber structure. The labeled polyclonal antibodies 14 used as reagents, which are brought into contact with the serum antigens 15 contained in the drop of serum brought into contact with the pellet containing the reagent 14, form a labeled antibody-antigen complex 10. As a blood which is positive in VDRL antigens contains about 200 picograms thereof per 50-microliter drop, the 500 picograms of labeled antibodies introduced into the upper stage 13 are sufficient to capture the serum antigens 15; moreover, this excess of antibodies has an effect on accelerating the Ag-Ab reaction. In fact, of the 500 picograms of labeled antibodies 14 of the upper stage 13, 200 picograms will bind to the serum antigens 15 to form the Ag-Ab complex 10, which will not bind to the solid phase consisting of the microspheres 5 of the middle stage 11. These microspheres (5 μl) of "Magnogel" (IBF) have a coating of VDRL-LATEX antigen (1 ng/5 μl) on protein A+-glutaraldehyde (IBF reagent) and VDRL (Diag. Pasteur Code 52675). As soon as the gelatin of the membrane 3 has been lysed, 300 picograms of labeled antibodies 14 which remain free will bind to the VDRL-LATEX antigens carried by the microbeads 5 of the middle stage 11, whilst the 200 picograms of labeled antibodies saturated by the serum antigens, 10, will pass through the lower membrane 3' (identical to the membrane 3), as soon as the gelatin which is blocking its pores has been lysed, to reach the lower stage 16, which is the disclosure zone containing the substrate (S) advantageously consisting of stabilized 3,3',5,5'-tetramethylbenzidine (ICN—MILES LAB.) on an appropriate support, for example Whatman no. 1 paper; the complex 10 gives a color reaction (12) by combining with the substrate (S); the coloration can appear with only 20 picograms if the substrate contains the glucose oxidase/β-D-glucose complex in addition to 3,3',5,5'-TMB, the said complex producing hydrogen peroxide in contact with serum, thereby making it possible to intensify the coloration.

Figure 3:
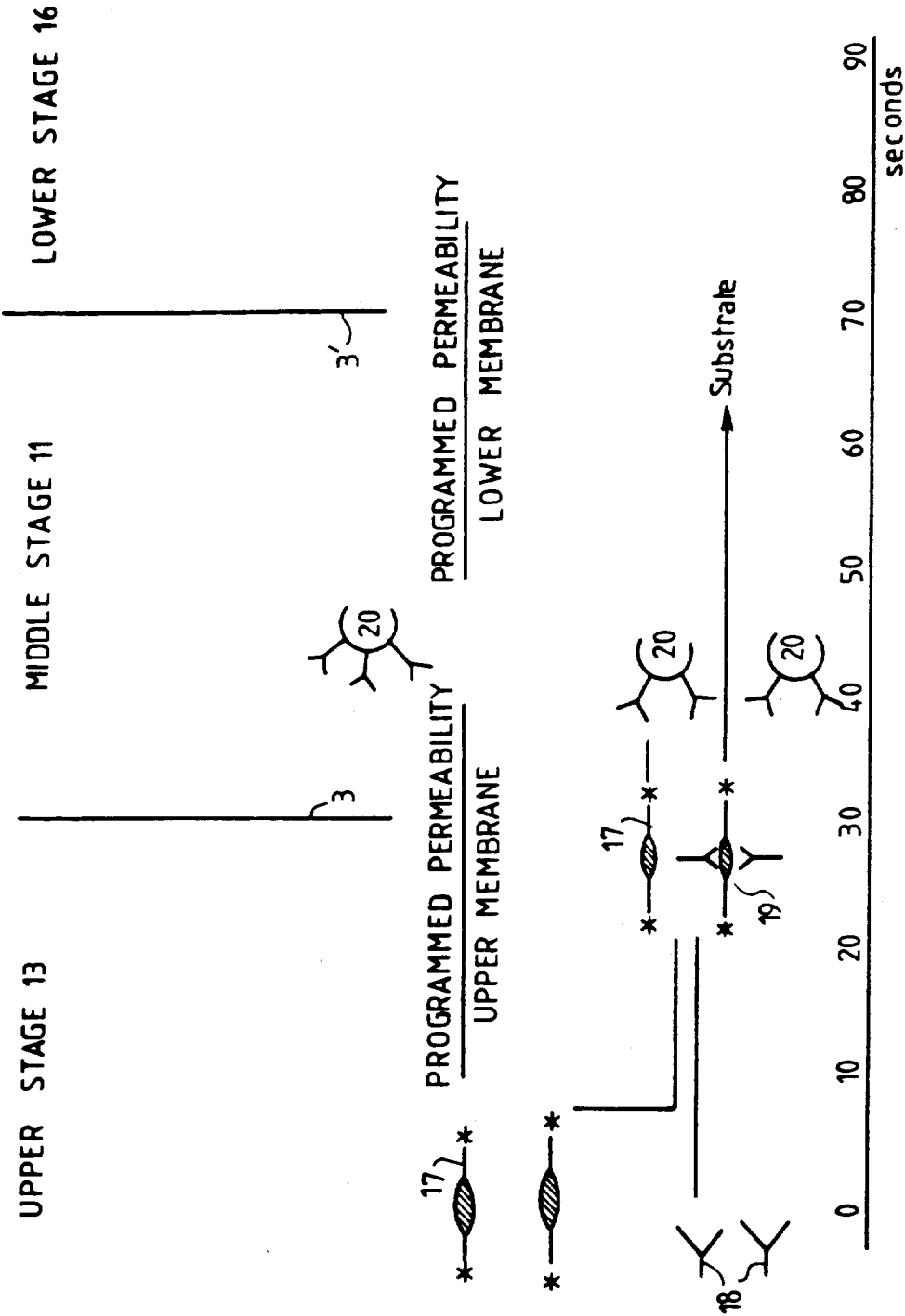
FIG. 3 shows a diagram of the steps of the method for the qualitative determination of the presence of antibodies.

FIG. 3 illustrates the qualitative assay of antibodies where a positive reaction is obtained: after about 30 seconds, all the labeled antigens are saturated by the serum antibodies, after which the upper membrane 3 is lysed, allowing all the antibody-labeled antigen complexes to pass through to the microspheres of the middle stage, to which unlabeled antibodies of the same kind as the antibodies to be detected are bound. As the epitopes (antigenic sites) are saturated by the serum antibodies, they are not recognized by the antibodies bound to the microspheres and they pass into the disclosure zone, where they react with the substrate to give a color reaction.

The Example illustrated in FIG. 3 applies more particularly to the detection of toxoplasmosis antibodies.

As reagent consisting of labeled antigens, the upper stage 13 receives toxoplasmosis antigens (Diag. Pasteur Code 52721) which are advantageously lyophilized (250 picograms) and are labeled with peroxidase (MERCK). The lyophilized pellet containing the Ags 17 also contains 5 units of collagenase (Collagenase Clostridium from Calbiochem). The membrane 3, which is advantageously supported by a glass fiber structure, is of the same type as that described in connection with FIG. 2. The labeled antigens 17 used as reagent, which are brought into contact with the (polyclonal) serum antibodies 18 contained in the drop of serum brought into contact with the pellet containing the reagent 17, form a labeled antigen-serum antibody complex 19. As a blood which is positive in antitoxoplasmosis antibodies contains 100 to 150 picograms thereof, the 250 picograms of labeled antigens 17 saturate these serum antibodies 18 and will prevent them from binding to the microbeads (5 μl)20—such as microbeads of "Magnogel"](IBF) having a coating of antitoxoplasmosis antibodies (1 ng/5 μl) on protein A+glutaraldehyde (IBF reagents; Institut Pasteur antibodies)—which are present in the middle state 11. As soon as the membrane 3 has been rendered permeable by lysis of the gelatin blocking its pores, the labeled antigens 17 which are not saturated by the serum antibodies 18 bind to the antibodies supported by the microbeads 20, whilst the labeled antigen-antibody complexes 21 pass through the lower membrane 3', as soon as it in turn has been rendered permeable, and combine with the substrate (S), which can be the same as in Example 2, to give a coloration which can be intensified, if appropriate, in the manner described in connection with FIG. 2.

Figure 4:
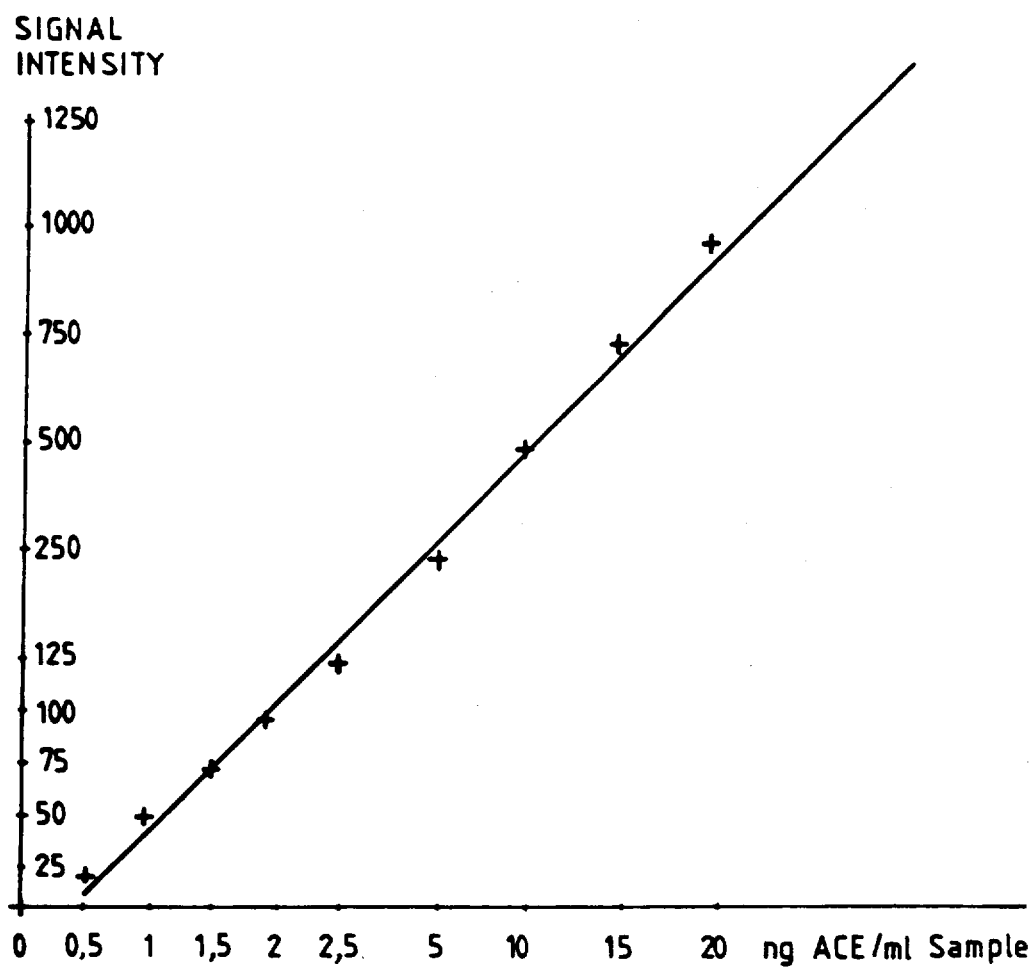
FIG. 4 shows the graph for the quantitative assay of the ACE present in human serum.

FIG. 4 shows a graph for the assay of ACE contained in samples of human serum.

The samples tested have a volume of 50 μliters. 10 samples of the same volume of test human serum and one sample of test human serum not containing ACE are treated in the following manner; a sample is poured onto the lyophilized pellet 1, which is supported by the membrane 3 and which contains 1250 picograms of peroxidase-labeled murine IgG1 directed against epitope 328.C of ACE.

After 30 seconds, all the labeled antibodies have been saturated by the serum antigens. The lysis by collagenase of the membrane 3, which is made of gelatin (reinforced with a glass fiber network), does not take place until these 30 seconds have elapsed, which causes the serum containing the labeled antibodies saturated by the serum antigens to flow into the second reaction zone, where they are brought into contact with the microbeads of the layer 5, coated with the same antigens. They are not retained by the antigens coating the microbeads 5 because the Fab sites of the labeled antibodies are saturated by the serum antigens; the enzyme present in the fluid passing through the second reaction zone then lyzes the second membrane 3', zone; in this zone, all the labeled antibodies bound to the serum antigens come into contact with the pellet of substrate, which is 3,3',5,5'-tetramethylbenzidine, and cause a quasi-immediate coloration in the presence of peroxidase. A narrow strip placed under the device according to the invention collects the filtration product and thus reveals the response signal which indicates the amount of labeled material passing through the microbeads.

The different concentrations of ACE in the sample analyzed, which are 0.5, 1, 1.5, 2, 2.5, 5, 10, 15 and 20 nanograms of ACE/ml of serum, i.e. 25, 50, 75, 100, 125, 250, 500, 750 and 1000 picograms of ACE in the 50 μl of sample to be assayed, are shown in FIG. 4.

By virtue of the very low detection thresholds afforded by the device and method according to the present invention, it is possible to carry out determinations, within the framework of the present invention, with a single 50 μl drop of blood.

It is also possible to carry out several diagnoses at the same time by using micropheres carrying different diagnostic labels.

The sensitivity of the assays is of the order of 5 to 125 picograms, depending on the sensitivity of the monoclonal antibody used: it is for this reason that the use of ultraspecific monoclonal antibodies is recommended.

As already stated earlier, the successive stages of the device according to the present invention constitute phases having different affinities for water; thus the upper stage is an absorption phase, the middle stage is a desorption phase and the lower stage is an absorption phase. This alternation is achieved, in the Example described, by establishing an osmotic glucose gradient. The result is that all the liquids are sucked towards the substrate of the lower stage, whereas, in the case of a negative reaction, only the labeled material is retained on the microspheres.

As is apparent from the foregoing description, the invention is in no way limited to the ways of carrying it out, the embodiments and the methods of application which have now been described more explicitly; on the contrary, it encompasses all the variants thereof which may occur to those skilled in the art, without departing from the framework or the scope of the present invention.

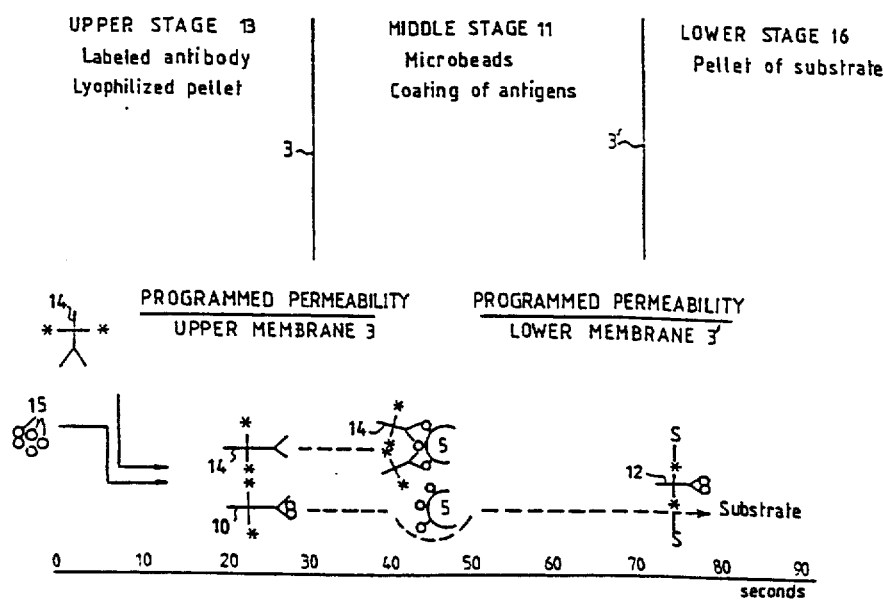

What is claimed is:

1. A device for rapid detection of the presence of a reactive ligand in a fluid test sample, comprising:
   a first reaction zone for receiving the fluid test sample and containing a temporarily impermeable first membrane, a labeled reagent capable of binding to the reactive ligand to be detected, and permeating means for rendering said first membrane permeable;
   a second zone, separate from said first reaction zone and temporarily isolated by said first membrane, said second zone containing a solid phase having bound thereto an unlabeled reference reagent capable of recognizing and retaining labeled reagent from said first zone which has not bound to the reactive ligand to be detected, and a second temporarily impermeable membrane opposite from said first membrane; and
   a third reaction zone, separate from said second reaction zone and at least temporarily isolated therefrom by said second membrane, said third reaction zone including disclosing means for disclosing the presence or absence of said labeled reagent;
   wherein said permeating means comprises an enzyme capable of dissolving of lysing said first and second membranes, said enzyme of said permeating means being different from the label of said labeled reagent, and wherein said first and second membranes are made of a material which is impermeable for a period of time sufficient to enable a ligand-labeled reagent or labeled reagent-reference reagent reaction to occur and is subsequently permeable due to said permeating means to allow fluid to pass therethrough to a subsequent reaction zone.

2. The device according to claim 1 wherein said permeating means is incorporated in said first membrane.

3. The device according to claim 1 wherein said labeled reagent is in solid form within said first reaction zone and is supported by said first membrane.

4. The device according to claim 1 wherein said solid phase in said second reaction zone consists of an insoluble support to which said unlabeled reference reagent is bound and said unlabeled reference reagent corresponds to the ligand to be detected.

5. The device according to claim 1 wherein said labeled reagent is labeled with a material capable of reacting with a chromogenic substance to produce color, and wherein said disclosing means comprises a chromogenic substance which reacts with said labeled reagent when present in said third reaction zone to form a chromogen which can be read by colorimetry.

6. The device according to claim 1 wherein said disclosing means includes quantifying means for quantifying the presence of said labeled reagent in the third zone.

7. The device of claim 6 wherein said quantifying means is a spectrophotometer or a radioimmunoassay quantifying apparatus.

8. The device according to claim 1 wherein said reaction zones are superimposed to form an upper stage comprising said first reaction zone, a middle stage comprising said second reaction zone, and a lower stage comprising said third reaction zone.

9. A method for rapid detection of the presence of a reactive ligand in a fluid by means of the device of claim 1, which comprises the steps of:
- adding a sample of fluid for analysis to said first reaction zone and maintaining said sample in said first zone for a sufficient time to enable a ligand-labeled reagent reaction to occur between said labeled reagent and any reactive ligand in said sample;
- causing said first membrane to become permeable to the fluid after said ligand-reagent reaction has occurred by means of said permeating means, to thereby permit transfer of said fluid from said first reaction zone to said second zone;
- maintaining said fluid in said second reaction zone for a sufficient time to enable a labeled reagent-reference reagent reaction to occur between any of said unbound labeled reagent in said fluid and said unlabeled reference bound to the solid phase in said second zone;
- causing said second membrane to become permeable to the fluid, after the labeled reagent reference reagent reaction has occurred, by means of said permeating means, to thereby permit transfer of said fluid from said second reaction zone to said third reaction zone, said solid phase being retained in said second zone; and
- detecting the presence of said labeled reagent in said third zone by means of said disclosing means, wherein the presence of said labeled reagent indicates the presence of said reactive ligand.

10. A method in accordance with claim 9 wherein said first and second membranes are made of gelatin and said permeating means comprises collagenase.

11. The device according to claim 1, wherein said permeating means is in said first reaction zone, and not incorporated in said first membrane.

12. A device in accordance with claim 1, wherein said labeled reagent is labeled with a label which can be read by fluorescence, chemiluminescence or radioactivity.

13. A device in accordance with claim 1 wherein said first and second membranes are made of gelatin and said permeating means comprises collagenase.

14. A device for detecting the presence of a reactive ligand in a fluid test sample at a semi-quantitative level, comprising:
- a first reaction zone for receiving the fluid test sample and containing a temporarily impermeable first membrane, a predetermined quantity of unlabeled reagent capable of binding to the reactive ligand to be detected, and permeating means for rendering said first membrane permeable;
- an intermediate reaction zone containing a labeled reagent capable of binding to the reactive ligand to be detected, said intermediate zone being separated from said first reaction zone by said first membrane to prevent contact of the sample in said first reaction zone with said labeled reagent for a time sufficient to enable a ligand-unlabeled reagent reaction to occur;
- a second reaction zone, separate from said first and intermediate reaction zones, said second zone containing a solid phase having bound thereto an unlabeled reference reagent capable of recognizing and retaining labeled reagent from said intermediate zone which has not bound to the reactive ligand to be detected, and a second temporarily impermeable membrane; and
- a third reaction zone, separate from said second reaction zone and at least temporarily isolated therefrom by said second membrane, said third reaction zone including disclosing means for disclosing the presence or absence of said labeled reagent;
- wherein said permeating means comprises an enzyme capable of dissolving or lysing said first and second membranes, said enzyme of said permeating means being different from the label of said labeled reagent, and wherein said first and second membranes are made of a material which is impermeable for a first period of time sufficiently to enable a ligand-unlabeled reagent or labeled reagent - reference reagent reaction to occur and is subsequently permeable due to said permeating means to allow fluid to pass therethrough to a subsequent reaction zone,
- whereby detection of the presence of labeled reagent by said disclosing means indicates the presence of the reactive ligand in the test sample in a quantity greater than the known quantity of unlabeled reagent in said first reaction zone.

15. The device according to claim 14 wherein said intermediate zone comprises at least one layer of vesicular structures having at least one labeled reagent which is capable of being released by said permeating means.

16. The device according to claim 14 wherein said intermediate zone is formed by an intermediate membrane intercalated between said first membrane and said second reaction zone, said labeled reagent being present between said first and intermediate membranes.

17. A device according to claim 14 wherein said reaction zones are superimposed to form an upper stage containing said first reaction zone, an intermediate stage below said upper stage, a middle stage below said intermediate stage, comprising said second reaction zone, and a lower stage comprising said third reaction zone.

18. A device in accordance with claim 14 wherein said first and second membranes are made of gelatin and said permeating means comprises collagenase.

19. A method for rapid detection of the presence of a reactive ligand in a fluid at a semi-quantitative level, by means of the device of claim 14, which comprises the steps of:
- adding a sample of fluid for analysis to said first reaction zone and maintaining said sample in said first reaction zone for a sufficient time to enable a ligand-unlabeled reagent to occur between said predetermined quantity of unlabeled reagent and any reactive ligand in said sample;
- subsequently causing said fluid to contact said labeled reagent in said intermediate reaction zone after said ligand-unlabeled reagent reaction has occurred in said first reaction zone to enable a ligand-labeled reagent reaction to occur between said labeled reagent and any reactive ligand remaining in said samples;

after said ligand-labeled reagent reaction has occurred, transferring said fluid from said intermediate reaction zone to said second reaction zone;

maintaining said fluid in said second reaction zone for a sufficient time to enable a labeled reagent-reference reagent reaction to occur between any of said unbound labeled reagent in said fluid and said unlabeled reference reagent bound to the solid phase in said second zone;

causing said second membrane to become permeable to the fluid after said labeled reagent reference reagent reaction has occurred, by means for said permeating means, to thereby permit transfer of said fluid from said second reaction zone to said third reaction zone, said solid phase being retained in said second zone; and detecting the presence of said labeled reagent in said third zone by means of said disclosing means, whereby detecting of the presence of labeled reagent in said third zone indicates the presence of the reactive ligand in the test sample in a quantity greater than the known quantity of unlabeled reagent in said first reaction zone.

20. A method in accordance with claim 19 wherein said first and second membranes are made of gelatin and said permeating means comprises collagenase.

* * * * *

UNITED STATES PATENT AND TRADEMARK OFFICE
CERTIFICATE OF CORRECTION

PATENT NO. : 5,217,905
DATED : June 8, 1993
INVENTOR(S) : Marchand, et al

It is certified that error appears in the above-indentified patent and that said Letters Patent is hereby corrected as shown below:

The title page, showing an illustrative figure, should be deleted and substitute therefor the attached title page.

The drawing sheet, consisting of Figure 1, should be deleted and replaced with Figure 1, as shown on the attached page.

The drawing sheet, consisting of Figure 2, should be deleted and replaced with Figure 2, as shown on the attached page.

Signed and Sealed this

Eleventh Day of October, 1994

Attest:

BRUCE LEHMAN

Attesting Officer     Commissioner of Patents and Trademarks

United States Patent [19]

Marchand et al.

[11] Patent Number: 5,217,905
[45] Date of Patent: Jun. 8, 1993

[54] DEVICE AND METHOD FOR THE RAPID QUALITATIVE AND QUANTITATIVE DETERMINATION OF THE PRESENCE OF A REACTIVE LIGAND IN A FLUID

[75] Inventors: Joseph Marchand, Verrieres Le Buisson; Jacques Toledano, Paris, both of France

[73] Assignees: Compagnie Oris Industrie S.A., Gif-Sur-Yvette; Cistest, Paris, both of France

[21] Appl. No.: 220,895

[22] Filed: Jul. 18, 1988

[30] Foreign Application Priority Data

Apr. 28, 1988 [FR] France ................... 88 05668

[51] Int. Cl.⁵ ............... G01N 33/53; G01N 33/558
[52] U.S. Cl. ............................ 436/518; 422/56; 422/57; 422/58; 435/7.92; 435/7.93; 435/805; 435/969; 435/970; 435/971; 436/170; 436/805; 436/810
[58] Field of Search ......... 436/810, 170, 805, 518; 435/7.92, 7.93, 805, 960, 969, 970, 971; 422/56, 58, 57

[56] References Cited

U.S. PATENT DOCUMENTS

| | | | |
|---|---|---|---|
| 4,446,232 | 5/1984 | Liotta | 435/805 |
| 4,522,786 | 6/1985 | Ebersole | 422/56 |
| 4,668,619 | 5/1987 | Greenquist et al. | 422/56 |
| 4,743,542 | 5/1988 | Graham, Jr. et al. | 436/534 X |
| 4,791,055 | 12/1988 | Boguzlash et al. | 436/546 X |
| 4,803,170 | 2/1989 | Stanton et al. | 436/514 X |

*Primary Examiner*—David Saunders
*Assistant Examiner*—Christopher L. Chin
*Attorney, Agent, or Firm*—Browdy and Neimark

[57] ABSTRACT

A device for the rapid qualitative and quantitative determination of the presence of a reactive ligand in a fluid.

This device comprises a first reaction zone in which there is an at least temporarily impermeable membrane designed to receive a sample of test fluid and to be associated with at least one labeled reagent; a second reaction zone which is bounded on the one hand by the said membrane and on the other by a second at least temporarily impermeable membrane comprising a solid phase containing a reference reagent; and a third reaction zone which contains means for developing the reaction.

A method for the rapid qualitative and quantitative determination of the presence of a reactive ligand in a fluid.

Applications to the detection of the presence, in a biological fluid, of antibodies or antigens in particular.

20 Claims, 3 Drawing Sheets

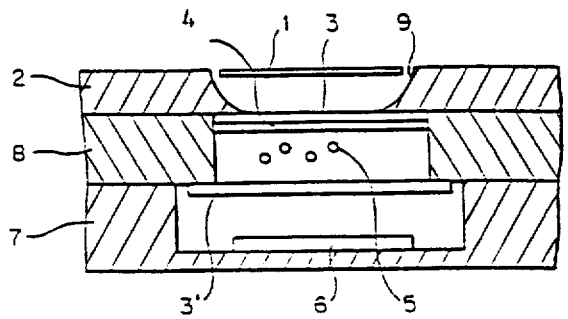

UNITED STATES PATENT AND TRADEMARK OFFICE
CERTIFICATE OF CORRECTION

PATENT NO. : 5,217,905

DATED : June 8, 1993

INVENTOR(S) : Marchand, et al

It is certified that error appears in the above-indentified patent and that said Letters Patent is hereby corrected as shown below:

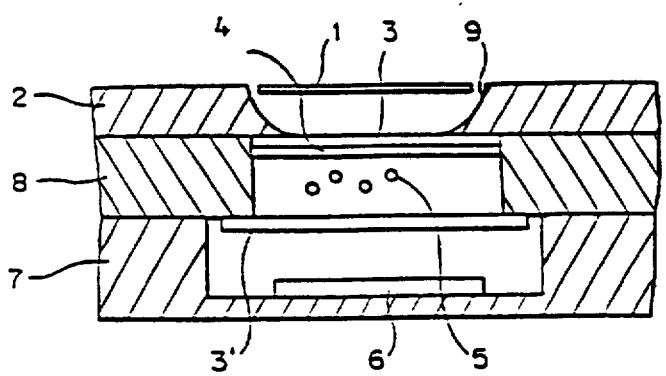

FIG.1

UNITED STATES PATENT AND TRADEMARK OFFICE
CERTIFICATE OF CORRECTION

PATENT NO. : 5,217,905

DATED : June 8, 1993

INVENTOR(S) : Marchand, et al

Page 4 of 4

It is certified that error appears in the above-indentified patent and that said Letters Patent is hereby corrected as shown below:

FIG. 2